United States Patent [19]

Stampa Díez Del Corral et al.

[11] Patent Number: 5,367,091
[45] Date of Patent: Nov. 22, 1994

[54] OPTICAL RESOLUTION OF DL-3-ACETYLTHIO-2-METHYLPROPIONIC ACID USING L-(+)-2-AMINOBUTANOL AS RESOLVING AGENT

[75] Inventors: Alberto Stampa Díez Del Corral; Maria del Carmen Onrubia Miguel; José Irurre Pérez, all of Barcelona, Spain

[73] Assignee: Medichem, S.A., Barcelona, Spain

[21] Appl. No.: 138,693

[22] Filed: Oct. 19, 1993

[30] Foreign Application Priority Data

Apr. 16, 1993 [ES] Spain ................................. 9300781

[51] Int. Cl.$^5$ ..................... C07C 307/06; C07B 57/00
[52] U.S. Cl. ...................................... 558/255; 564/303
[58] Field of Search ............................. 558/255

[56] References Cited

U.S. PATENT DOCUMENTS

| | | | |
|---|---|---|---|
| 4,224,457 | 9/1980 | Iwao et al. | |
| 4,294,775 | 10/1981 | McKinnie | 558/255 |
| 4,297,282 | 10/1981 | Ohashi et al. | 558/255 X |
| 4,325,886 | 4/1982 | Ohashi et al. | 558/255 |
| 4,346,045 | 8/1982 | De Heij | 558/255 |
| 4,559,178 | 12/1985 | Buzby, Jr. et al. | 558/255 X |
| 4,585,595 | 4/1986 | Houbiers | 558/255 |
| 5,001,251 | 3/1991 | MacManus et al. | 558/255 |
| 5,097,043 | 3/1992 | MacManus et al. | |

FOREIGN PATENT DOCUMENTS

| | | |
|---|---|---|
| 0008833 | 3/1980 | European Pat. Off. |
| 0105696 | 4/1984 | European Pat. Off. |
| 56-7756 | 1/1981 | Japan . |
| 2213818 | 8/1989 | United Kingdom . |

Primary Examiner—Mary C. Lee
Assistant Examiner—Michael G. Ambrose
Attorney, Agent, or Firm—Scully, Scott, Murphy & Presser

[57] ABSTRACT

This invention refers to a new process for the preparation of D-(—)-3-acetylthio-2-methylpropionic acid, an important intermediate in the synthesis of the antihypertensive Captopril, consisting of the resolution of the racemic mixture of said acid through formation of the mixture of the diastereomeric salts thereof, in an appropriate solvent, with the low molecular weight L-(+)-2-aminobutanol as a base, selective crystallization of the diastereomeric salt of D-(-)-3-acetylthio-2-methylpropionic acid with L-(+)-2-aminobutanol and release of the D-(—)-3-acetylthio-2-methylpropionic acid through displacement of the base with a stronger acid.

8 Claims, No Drawings

OPTICAL RESOLUTION OF DL-3-ACETYLTHIO-2-METHYLPROPIONIC ACID USING L-(+)-2-AMINOBUTANOL AS RESOLVING AGENT

FIELD OF THE INVENTION

This invention refers to a process for the preparation of D-(—)-3-acetylthio-2-methylpropionic acid, an important intermediate in the preparation of the hypertensive agent Captopril, based on the resolution of the racemic mixture of said acid with its enantiomer, L-(+)-3-acetylthio-2-methylpropionic acid.

PRIOR ART

It is well known that D-(—)-3-acetylthio-2-methylpropionic acid, which has the formula:

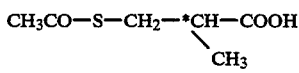

(henceforth D-AMPA), constitutes a very important intermediate in the industrial preparation of the antihypertensive Captopril, (2S)-1-(3-mercapto-2-methylpropionyl)-L-proline, since it permits the chiral centre, marked in the above formula with an asterisk, to be directly incorporated into the Captopril molecule, thereby circumventing the need to perform a double decomposition of the diastereomeric mixture in the final product.

The general method, consisting of resolving racemic mixtures of organic compounds replaced with some acid or basic group, through the formation of the diastereomeric addition salts with an enantiomer of an organic acid or base that also possesses chirality, is also well known. This general method takes advantage of the possibility that the two diastereomeric salts formed exhibit different solubility properties in a particular solvent system, thus permitting the separation of both diastereomeric salts through fractional crystallization.

In the industrial application of this general method to the resolution of the racemic mixture of a specific organic acid, such as DL-(±)-3-acetylthio-2-methylpropionic acid (henceforth DL-AMPA), different technical problems are posed for the man of the art which are difficult to resolve. Among these, it is possible to mention firstly and most importantly, the selection of an enantiomeric organic base which would provide a greater difference in the solubility of the diastereomeric salts formed in order to achieve an efficient fractional crystallization which would allow good enantiomer separation yields and optical purities at the lowest possible industrial cost.

To accomplish this objective, in addition to its ability to form diastereomeric salts with well differentiated solubilities, it is important that the enantiomeric base selected be easily accessible at a reasonable cost, and that, if possible, it have a low molecular weight since, given that the salt formation is produced under stoichiometric conditions, i.e., one mole per mole for the acid, this produces very important beneficial industrial effects. On the one hand, in order to separate a given quantity of racemic mixture, smaller quantities of base are required as the mixture's molecular weight is lower. On the other hand, the production process efficiency is noticeably improved for a given industrial facility since, evidently, when displacement of the diastereomeric salt to obtain D-AMPA must take place, larger quantities of this acid will be obtained per reaction volume unit in the case that the majority component by weight of said salt were D-AMPA. Consequently, the base recovery process will also require smaller volumes.

Another important aspect which the man of the art must consider is linked to the selection of the base and consists of selecting the solvent system in which the fractional crystallization should be performed.

Of course, an industrially efficient process for the preparation of D-(-(—)-3-acetylthio-2-methylpropionic acid should also consider the racemization of the undesirable isomer, L-(+)-3-acetylthio-2-methylpropionic acid (henceforth L-AMPA), so that it can be reused in the separation phase.

The economic and industrial importance of the antihypertensive Captopril has caused the problem of the double decomposition of the racemic mixture of DL-AMPA to be the subject of various patents.

Example 8 of U.S. Pat. No. 4,224,457 (Iwao et al.) describes the utilization of the enantiomer base D-(—)-1,2-diphenylethylamine, of molecular weight 197, utilizing acetone as a solvent.

Example 1 of U.S.-Pat. No. 4.325.886 (Ohashi et el.) proposes the utilization of L-2-amino-1,1-diphenylpropanol, of molecular weight 227, as an enantiomer base with water as a solvent.

U.S. Pat. No. 5.097.043 (MacMenus et el.) proposes the utilization of naphthylmethyl-o-methylbenzylamines of high molecular weight as enantiomer bases, for example, substituted D-(+)-N-(1-naphthylmethyl)-o-methylbenzylamine, with a molecular weight of 261.

The abstract compiled in CA,95:24281e (Chemical Abstracts), corresponding to the Japanese patent application JP56007756, describes the use of L-1-phenyl]-2-(4-chlorophenyl) ethylamine, of molecular weight 231.5 employing acetonitrile as a solvent.

EP-A-O 105 696 (Hasatoshi et al.) proposes the use of substituted phenylalaninols as the enantiomer base, specifically, in examples 6 and 11, N-isopropyl]-L-phenylalaninol, of molecular weight 193, in an ethyl acetate medium.

Other related references are, for example: CA,95:62706e, in which the use of L-2-(4-methylphenyl)-1-phenylethylamine, of molecular weight 211, as the enantiomer base is described; and CA,112:98027t, which uses D-(+)-N-(α-naphthyl) methyl-2phenyl propylamine, of molecular weight 275.

As can be observed, the enantiomer bases employed up until now are of rather high molecular weight, which means that the problem of finding a process for preparing D-AMPA through resolution of the racemic DL-AMPA which permits the utilization of a low molecular weight enantiomeric base and which still gives good chemical yields and optical purity remains unresolved.

This invention resolves this problem through a process based on the use of L-(+)-2-aminobutanol (henceforth L-AB), of molecular weight 89, as the enantiomer base; this also provides excellent chemical yields and optical purities in the preparation of D-AMPA.

The solution discovered is rather surprising and unexpected since, in accordance with that which has been described in EP-B-O 008 833 (Houbiers), the utilization of D-(—)-2-aminobutanol (henceforth D-AB) is not efficient enough in the resolution of DL-AMPA, since, in order to obtain good results, it is necessary to carry out the resolution with D-AB on a precursor, DL-3-benzoylthio-2-methylpropionic acid and to later perform the replacement of the benzoyl group with an acetyl group to give D-AMPA. In view of the foregoing, the man of the art would not be able to predict that L-AB would be effective in the resolution of DL-AMPA since its enantiomer D-AB is not.

SUMMARY OF THE INVENTION

This invention consists of a process for the preparation of D-(−)-3-acetylthio-2-methylpropionic acid which permits the separation of the racemic mixture of DL-(±)-3-acetylthio-2-methylpropionic acid with excellent chemical yields and optical purity and at the same time provides industrial benefits with respect to costs and simplicity, due to the use of a low molecular weight enantiomer base as a resolution agent.

DETAILED DESCRIPTION OF THE INVENTION

The process for the preparation of D-AMPA of the invention is essentially characterized by forming, in an appropriate solvent, the mixture of the two possible diastereomeric salts of D-AMPA with L-AB, selectively crystallizing the diastereomeric salt of D-AmPA with L-AB, separating this diastereomeric salt and releasing D-AMPA through the displacement of this salt with a stronger acid.

It is especially preferable in view of the objectives of this invention that the solvent employed be an aliphatic ester of low boiling point, in which low boiling point is understood to be lower than 125° C. Examples of such solvents are methyl acetate, ethyl acetate, methyl propionate, ethyl propionate, methyl butyrate; among these, ethyl acetate is especially preferred.

Other types of useful solvents are, for example, ethanol, methanol and acetone, although they do not give as good results as the ones mentioned above.

It is advisable that the proportions between DL-AMPA and L-AB correspond to the stoichiometric proportions, although these proportions can vary slightly.

The salt formation can be performed at various temperatures between ambient temperature and the solvent's reflux temperature. In any regard, if the salt formation is performed at a low temperature, it is then helpful subsequently to heat the diastereomeric salt solution to a temperature between 50° C. and the solvent's reflux temperature in order to selectively crystallize the diastereomeric salt of D-AMPA through gradual cooling of the solution.

It is preferable to induce the onset of this crystallization through a seed consisting of a small quantity of crystals of the diastereomeric salt of D-AMPA and L-AB.

In this way, the D-AMPA salt obtained in the first crystallization already has a very high optical purity, in the order of 90%, and so only one additional recrystallization is required to achieve optical purities of D-AMPA, obtained through subsequent acidification of the salt, in the order of 99%.

The recrystallization of the D-AMPA salt obtained is not especially critical and can be performed in any appropriate solvent such as acetone, for example. Nor is the displacement of the salt for obtaining D-AMPA critical and it can be performed in an aqueous medium by adding a stronger acid than D-AMPA, for example, utilizing any type of mineral acid such as hydrochloric acid, sulphuric acid, etc.

As is obvious to any man of the art, most of the L-AB can be recovered through alkalinization of the mother liquids proceeding from the displacement of the diastereomeric salt, removal of the water by distillation, extraction of the L-AB from the residue with an appropriate solvent, for example, a short-chain aliphatic alcohol and distillation of the L-AB at reduced pressure.

It is also obvious to the man of the art that a significant part of the remaining L-AB and of the 3-acetylthio-2-methylpropionic acid rich in the undesired isomer L-AMPA can be recovered from the mother liquids proceeding from the first crystallization and from the recrystallization of· D-AMPA, using the same techniques already described.

The 3-acetylthio-2-methylpropionic acid rich in L isomer can be racemized through known techniques, such as the ones described in CA,94:120879f, consisting of hot treatment with different types of bases so that it can be used again in the preparation of D-AMPA through the process which is the subject of this invention.

In order to aid a better understanding of this invention, the following examples-which should not be interpreted as limitations to said invention- are presented.

EXAMPLE 1

Resolution of DL-(±)-3-acetylthio-2-methylpropionic Acid with L-(+)-2-aminobutanol 76.8 g (0.474 mole, of DL-(±)-3-acetylthio-2-methylpropionic acid were dissolved in 80 ml of ethyl acetate. At ambient temperature and under agitation, 42.19 g (0.474 mole) of L-(+)-2-aminobutanol were added and the temperature of the solution was raised to 60° C. Immediately afterwards, the solution was seeded with some pure salt crystals of D-(−)-3-acetylthio-2-methylpropionic acid. Stirring was maintained for five hours until the mixture reached ambient temperature. The crystallized salt was then filtered, washed with ethyl acetate and dried in an oven at 60° C. for five hours, thus obtaining 48.70 g of D-(−)-3-acetylthio-2-methylpropionic acid salt with $[\alpha]_D=24.4°$ (C=0.880, ethanol), optical purity 89%. The salt thus obtained was recrystallized from acetone obtaining 37.69 g, $[\alpha]_D=-27.5°$ (C=1.008, ethanol). The crystallization and recrystallization liquids were kept for subsequent recovery of L-(+)-2-aminobutanol and 3-acetylthio2-methylpropionic acid rich in L isomer.

EXAMPLE 2

Preparation of D-(−)-3-acetylthio-2-methylpropionic Acid and Recovery of L-AB

In 70 ml. of water, 37.6 g (0.15 mole) of the salt of D-(−)-3-acetylthio-2-methylpropionic acid were dissolved in L-(+)-2-aminobutanol and 26.2 ml of 6 N hydrochloric acid were then added. A denser phase than the aqueous was separated and extracted three times with 80 ml of dichloromethane each time. The organic phases were combined and dried over anhydrous magnesium sulphate and the solvent was removed at reduced pressure. The crude D-(−)-3-acetylthio-2-methylpropionic acid obtained was purified through fractional distillation at reduced pressure, withdrawing the fraction distilling at 110°-113° C. at 1 mm Hg. In this way, 22.60 g of D-(−)-3-acetylthio-2-methylpropionic acid were obtained with $[\alpha]_D = -46.0°$ (C=1.750, ethanol), giving an optical purity of 99%

The water was removed from the previously mentioned aqueous phase by distillation at reduced pressure. The residue was dissolved in 24 ml of water and treated with 26.2 ml of 6N sodium hydroxide. The water was then removed by distillation at reduced pressure and the residue was extracted three times with 24 ml of ethanol each time. The ethanol was removed by distillation at reduced pressure and the L-(+)-2-aminobutanol was purified through fractional distillation at reduced pressure, withdrawing the fraction distilling at 42°–45° C. at 1 mm Hg, thus obtaining 8.0 g of amine with $[\alpha]_D = +12.0°$ (C=0.987, ethanol).

EXAMPLE 3

Racemization of D-(−)-3-acetylthio-2-methylpropionic acid rich in L isomer

All of the crystallization and recrystallization liquids from example 1 were pooled and the solvent was removed at reduced pressure. In order to separate the 3-acetylthio-2-methylpropionic acid from the L-(+)-2-aminobutanol, a treatment analogous to the one described in Example 2 was performed. The L-(+)-2-aminobutanol was recovered in an analogous fashion to the one described in Example 2. The recovered 3-acetylthio-2-methylpropionic acid, enriched with L isomer, was dissolved in 400 ml of xylene and 34.53 g (0.18 mole) of tributylamine were then added. The mixture was refluxed with stirring for 24 hours, after which the solvent was removed at reduced pressure. The residue was then diluted in 250 ml of ethyl acetate and extracted two times with 150 ml E of 3%); aqueous hydrochloric acid each time. The organic phase was dried over anhydrous magnesium sulphate and the solvent was removed at reduced pressure. The oil 1 thus obtained was purified through fractional distillation at reduced pressure, withdrawing the fraction distilling at 120°–125° C. at 0.5–1 mm Hg thus giving 25.70 g of an oil with $[alpha]_D = +3.9°$ (c=1.192, ethanol).

What we claim is:

1. A process for the preparation of D-(−)-3-acetylthio-2-methylpropionic acid from its racemic mixture, comprising the following steps:
   i) forming, in an appropriate solvent, a mixture of the two possible diastereomeric salts of DL-(+) -3-acetylthio-2-methylpropionic acid with the enantiomer base L-(+)-2-aminobutanol;
   ii) selectively crystallizing the diastereomeric salt of D-(−)-3-acetylthio-2-methylpropionic acid with L-(+)-2-aminobutanol;
   iii) separating said diastereomeric salt; and
   iv) releasing the D-(−)-3-acetylthio-2-methylpropionic acid through the displacement of the base with a stronger acid.

2. The process of claim 1, wherein the solvent is an aliphatic ester with a boiling point lower than 125° C.

3. The process of claim 2, wherein the solvent is ethyl acetate.

4. The process of claim 1, wherein the proportions employed are close to the stoichiometric proportions of DL-(±)-3-acetylthio-2-methylpropionic acid and L-(+)-2-aminobutanol.

5. The process of claim 1, wherein the selective crystallization is performed through gradual cooling of the solution from a temperature between 50° C. and the solvent's reflux temperature and aiding the crystallization by adding a small quantity of crystals of the diastereomeric salt of D-(−)-3-acetylthio-2-methylpropionic acid with L-(+)-2-2-aminobutanol.

6. The process of claim 1, wherein the diastereomeric salt of the D-(−)-3-acetylthio-2-methylpropionic acid with L-(+)-2- aminobutanol, obtained in the selective crystallization is recrystallized in an appropriate solvent.

7. The process of claim 1, wherein the L-(+)-2-aminobutanol is recovered from the mother liquids proceeding from the different stages of the process through alkalinization and distillation at reduced pressure.

8. The process of claim 1, wherein the 3-acetylthio-2-methylpropionic acid, rich in L isomer, is recovered from the mother liquids proceeding from the selective crystallization and racemized through hot treatment with an appropriate base.

* * * * *

UNITED STATES PATENT AND TRADEMARK OFFICE
CERTIFICATE OF CORRECTION

PATENT NO. : 5,367,091
DATED : November 22, 1994
INVENTOR(S) : A. S. D. Del Corral, et al.

It is certified that error appears in the above-indentified patent and that said Letters Patent is hereby corrected as shown below:

```
Column 2, line 25 & 29:  "el."  should read  --al.--
Column 2, line 29:  "MacMenus"  should read
--MacManus--
Column 2, lines 30 & 32:  " -o- "  should read
-- -α- --
Column 2, line 36:  after "phenyl"  delete  --]--
Column 2, line 39:  "Hasatoshi"  should read
--Masatoshi--
Column 2, line 41:  after "N-isopropyl"  delete  --]--
Column 2, line 48:  "2phenyl"  should read  --2-phenyl--
Column 3, line 25:  "D-AmPA"  should read  --D-AMPA--
Column 4, lines 44 & 47:  "(C"  should read  --(c--
Column 4, line 49:  "3-acetylthio2"  should read
--3-acetylthio-2--
Column 5, lines 2 & 15:  "(C"  should read  --(c--
Column 5, line 36:  delete "E"
Column 5, line 39:  "delete "1"
```

Column 5, line 36: "3%);" should read –3%– .

UNITED STATES PATENT AND TRADEMARK OFFICE
CERTIFICATE OF CORRECTION

PATENT NO. : 5,367,091
DATED : November 22, 1994
INVENTOR(S) : A. S. D. Del Corral, et al.

It is certified that error appears in the above-indentified patent and that said Letters Patent is hereby corrected as shown below:

Column 6, line 5, Claim 1: "(+)" should read --($\pm$)--
Column 6, line 29, Claim 5: "2-2-aminobutanol" should read --2-aminobutanol--

Signed and Sealed this

Twenty-third Day of July, 1996

Attest:

BRUCE LEHMAN

Attesting Officer        Commissioner of Patents and Trademarks